United States Patent
Vodanovic

(10) Patent No.: US 7,535,560 B2
(45) Date of Patent: May 19, 2009

(54) METHOD AND SYSTEM FOR THE INSPECTION OF INTEGRATED CIRCUIT DEVICES HAVING LEADS

(75) Inventor: Bojko Vodanovic, Baie d'Urfe (CA)

(73) Assignee: Aceris 3D Inspection Inc., Baie d'Urfé (CA)

( * ) Notice: Subject to any disclaimer, the term of this patent is extended or adjusted under 35 U.S.C. 154(b) by 262 days.

(21) Appl. No.: 11/678,736

(22) Filed: Feb. 26, 2007

(65) Prior Publication Data

US 2008/0204732 A1    Aug. 28, 2008

(51) Int. Cl.
G01N 21/00    (2006.01)
(52) U.S. Cl. .................... 356/237.1; 356/394
(58) Field of Classification Search ............. 356/237.1, 356/394; 250/559.34, 559.22
See application file for complete search history.

(56) References Cited

U.S. PATENT DOCUMENTS

| | | | |
|---|---|---|---|
| 5,406,372 A | 4/1995 | Vodanovic et al. |
| 5,440,391 A | 8/1995 | Smeyers et al. |
| 5,465,152 A | 11/1995 | Bilodeau et al. |
| 5,479,252 A | 12/1995 | Worster et al. |
| 5,580,163 A | 12/1996 | Johnson, II |
| 5,617,209 A | 4/1997 | Svetkoff et al. |
| 5,818,959 A | 10/1998 | Webb et al. |
| 5,956,134 A | 9/1999 | Roy et al. |
| 6,118,540 A | 9/2000 | Roy et al. |
| 6,134,013 A | 10/2000 | Sirat et al. |
| 6,167,148 A | 12/2000 | Calitz et al. |
| 6,205,238 B1 | 3/2001 | Ma |
| 6,324,298 B1 | 11/2001 | O'Dell et al. |
| 6,547,409 B2 | 4/2003 | Kiest et al. |
| 6,661,515 B2 | 12/2003 | Worster et al. |
| 6,671,397 B1 | 12/2003 | Mahon et al. |
| 6,731,383 B2 | 5/2004 | Watkins et al. |
| 6,750,974 B2 | 6/2004 | Svetkoff et al. |
| 6,765,666 B1 | 7/2004 | Guest et al. |
| 6,771,807 B2 | 8/2004 | Coulombe et al. |
| 6,773,935 B2 | 8/2004 | Watkins et al. |
| 6,778,282 B1 | 8/2004 | Smets et al. |
| 6,820,349 B2 | 11/2004 | Peine |
| 6,826,298 B1 | 11/2004 | O'Dell et al. |
| 6,870,609 B2 | 3/2005 | Watkins et al. |
| 6,882,415 B1 | 4/2005 | Watkins et al. |
| 6,915,006 B2 | 7/2005 | Beaty et al. |
| 6,934,019 B2 | 8/2005 | Geffen et al. |
| 6,937,753 B1 | 8/2005 | O'Dell et al. |
| 6,947,588 B2 | 9/2005 | Sim |
| 6,970,238 B2 | 11/2005 | Gerhard et al. |
| 6,970,287 B1 | 11/2005 | Watkins et al. |
| 7,019,826 B2 | 3/2006 | Vook et al. |
| 7,019,841 B2 | 3/2006 | Mathur |

(Continued)

FOREIGN PATENT DOCUMENTS

JP    63109307 A2    5/1988

(Continued)

*Primary Examiner*—Roy M Punnoose
(74) *Attorney, Agent, or Firm*—Goudreau Gage Dubuc

(57) ABSTRACT

The invention relates to optical inspection of integrated circuit devices, such as QFP and TSOP devices. There are provided methods of inspecting objects, such as integrated circuit devices, using a single laser triangulation system oriented in a fixed direction, where the given inspection system rotates the inspection tray for scanning the objects placed therein in different directions.

16 Claims, 8 Drawing Sheets

U.S. PATENT DOCUMENTS

| | | |
|---|---|---|
| 7,023,559 B1 | 4/2006 | Coulombe et al. |
| 7,024,031 B1 | 4/2006 | Castellanos-Nolasco et al. |
| 7,034,272 B1 | 4/2006 | Leonard et al. |
| 7,081,953 B2 | 7/2006 | Uto et al. |
| 7,397,550 B2 * | 7/2008 | Hackney et al. .......... 356/237.1 |
| 2007/0003129 A1 | 1/2007 | Matsuda |

FOREIGN PATENT DOCUMENTS

WO  WO 2006/065437 A2  6/2006

* cited by examiner

__ US 7,535,560 B2 __

METHOD AND SYSTEM FOR THE INSPECTION OF INTEGRATED CIRCUIT DEVICES HAVING LEADS

FIELD OF THE INVENTION

The present invention relates to a method and system for the inspection of integrated circuits having leads.

BACKGROUND OF THE INVENTION

A quad flat package or QFP is an integrated circuit comprising a rectangular or a square body, generally made of either plastic or ceramic material, from whose periphery gull wing shaped leads extend. QFP chip packages have gull wing type leads on four sides. As technology advances, chips become smaller in size and number of leads thereon becomes greater. As a result, size of leads and clearance there between has become smaller and smaller.

On the other hand, it is necessary for all leads on a chip to have proper clearance, not to be bent out of shape and to be coplanar. This means, when placed on a flat surface (for example, a printed circuit board), all leads should preferably be touching the flat surface or at least display a minimum clearance to allow proper soldering of the leads to the surface when required. QFP leads that lack the aforementioned cannot be properly soldered resulting in higher manufacturing costs and, if not detected early in the manufacturing process, even costlier failures in the field.

QFP chips are generally packaged in groups of 12 or more and shipped in standard trays to prevent damage of the very fragile leads. QFP chips are generally inspected inside their respective standard trays. In addition to facilitating handling (complete trays instead of individual devices), such an approach reduces the possibility of further lead damage by the inspection system as there is no device manipulation. QFP inspection consists of inspecting different lead characteristics, such as clearance between adjacent leads, bent conditions, overall lead position (geometry) and co-planarity.

One problem with QFP devices sitting in a tray pocket is that, due to lead occlusions, it is nearly impossible to scan lead tips with a single laser triangulation system oriented in a fixed direction. In fact, a typical laser triangulation system has to scan in two transversal axes, in parallel with lead main axes.

Prior art scanning systems display different scanning techniques as a solution to the above problem, such as (1) using two different laser triangulation systems (one for each of the two transversal directions and switching between them depending on a scanning direction) or (2) using a single laser triangulation system with a rotating head (and rotating the head as a function of the scanning direction) (see U.S. Pat. No. 5,406,372). Another technique used is a single laser triangulation system oriented at 45° of the two transversal directions to scan in one direction only.

All of the aforementioned scanning techniques have certain drawbacks, such as high costs (when two laser triangulation systems or a rotating head is used), accuracy problems (when a rotating head is used) and reduced efficiency in case of long leads with short tips (QFP208 devices) (when a laser system oriented at 45° is used).

Besides the aforementioned scanning techniques, another prior art technique consists of scanning QFP devices in an upside-down position (also known as a "dead bug" position), however most tray designs cannot guarantee such a position for QFP devices. Moreover, placing QFP devices in a "dead bug" position inside a tray risks damaging their leads when stacking trays.

SUMMARY OF THE INVENTION

In order to over come the above and other drawbacks there is provided a method of inspecting an object. The method comprises placing the object on a support and placing the support in a scanner comprising a 3D scanning system, scanning the object in a first direction using the 3D scanning system to obtain a first profile line data set of the object, rotating the support with respect to the first direction to scan the object in a second direction, the rotation of the support having an effect of displacing the object with respect to the support, scanning the device in the second direction using the 3D scanning system to obtain a second profile line data set of the object, identifying a common feature in the first and second profile line data sets of the object, referencing the obtained first and second profile line data sets with respect to the common feature, and combining the first and second profile line data sets referenced with respect to one another to construct a model of the object.

There is also provided a method of inspecting an integrated circuit comprising a rectangular package and leads arranged along a first and second non-parallel edges. The method comprises placing the integrated circuit in a scanner comprising a 3D scanning system, scanning the leads along the first edge in a first direction using the 3D scanning system to obtain a first profile line data set of the object, rotating the integrated circuit with respect to the first direction to scan the object in a second direction, scanning the leads along the second edge in the second direction using the 3D scanning system to obtain a second profile line data set of the integrated circuit, identifying a common feature in the first and second profile line data sets of the integrated circuit, referencing the obtained first and second profile line data sets with respect to the common feature, and combining the first and second profile line data sets referenced with respect to one another to construct a model of the integrated circuit.

Additionally, there is provided a method of inspecting different types of integrated circuit devices having leads. The method comprises providing a scanner comprising: a 3D scanning system having a predetermined scan direction and a tray manipulation system for receiving a tray of predetermined rectangular dimensions and orientation carrying integrated circuit devices, positioning the tray within the 3D scanning system, and for transferring the tray from the scanner to a downstream tray handling device following inspection, using the tray manipulation system to place a first tray containing a first type of integrated circuit devices having leads in the scanner, and scanning the first type of devices in a first direction with the 3D scanning system operating in the predetermined scan direction, removing the first tray from the scanner using the tray manipulation system, using the tray manipulation system to place a second tray containing a second type of integrated circuit devices in the scanner and to rotate the second tray, and scanning the second type of devices in a second direction with the 3D scanning system operating in the predetermined scan direction, removing the second tray from the scanner, the tray manipulation system transferring the first tray and the second tray to the downstream tray handling device in a same orientation.

Furthermore, there is provided a method of manufacturing a product. The method comprises placing the object on a support and placing the support in a scanner comprising a 3D scanning system, scanning the object in a first direction using the 3D scanning system to obtain a first profile line data set of the object, rotating the support with respect to the first direction to scan the object in a second direction, the rotation of the support having an effect of displacing the object with respect to the support, scanning the device in the second direction using the 3D scanning system to obtain a second profile line data set of the object, identifying a common feature in the first and second profile line data sets of the object, referencing the obtained first and second profile line data sets with respect to the common feature, combining the first and second profile line data sets referenced with respect to one another to construct a model of the object, determining from the model a fitness of the product and recycling or releasing the product as a function of the fitness.

In addition to the above there is provided a method of manufacturing different types of products. The method comprises providing a scanner comprising: a 3D scanning system having a predetermined scan direction and a tray manipulation system for receiving a tray of predetermined rectangular dimensions and orientation carrying integrated circuit devices, positioning the tray within the 3D scanning system, and for transferring the tray from the scanner to a downstream tray handling device following inspection, using the tray manipulation system to place a first tray containing a first type of products in the scanner, and scanning the first type of products in a first direction with the 3D scanning system operating in the predetermined scan direction, where the first type of products are a first type of integrated circuit devices having leads, constructing a model of the first type of products, determining from the model a fitness of the first type of products, recycling or releasing the first type of products as a function of the fitness, removing the first tray from the scanner using the tray manipulation system, using the tray manipulation system to place a second tray containing a second type of products in the scanner and to rotate the second tray, and scanning the second type of products in a second direction with the 3D scanning system operating in the predetermined scan direction, where the second type of products are a second type of integrated circuit devices having leads, constructing a model of the second type of products, determining from the model a fitness of the second type of products, recycling or releasing the second type of products as a function of the fitness, removing the second tray from the scanner, the tray manipulation system transferring the first tray and the second tray to the downstream tray handling device in a same orientation.

BRIEF DESCRIPTION OF THE DRAWINGS

Further features and advantages of the invention will become more readily apparent from the following detailed description of the invention as illustrated by way of examples in the appended drawings wherein.

DETAILED DESCRIPTION OF THE ILLUSTRATIVE EMBODIMENTS

Figure 1:
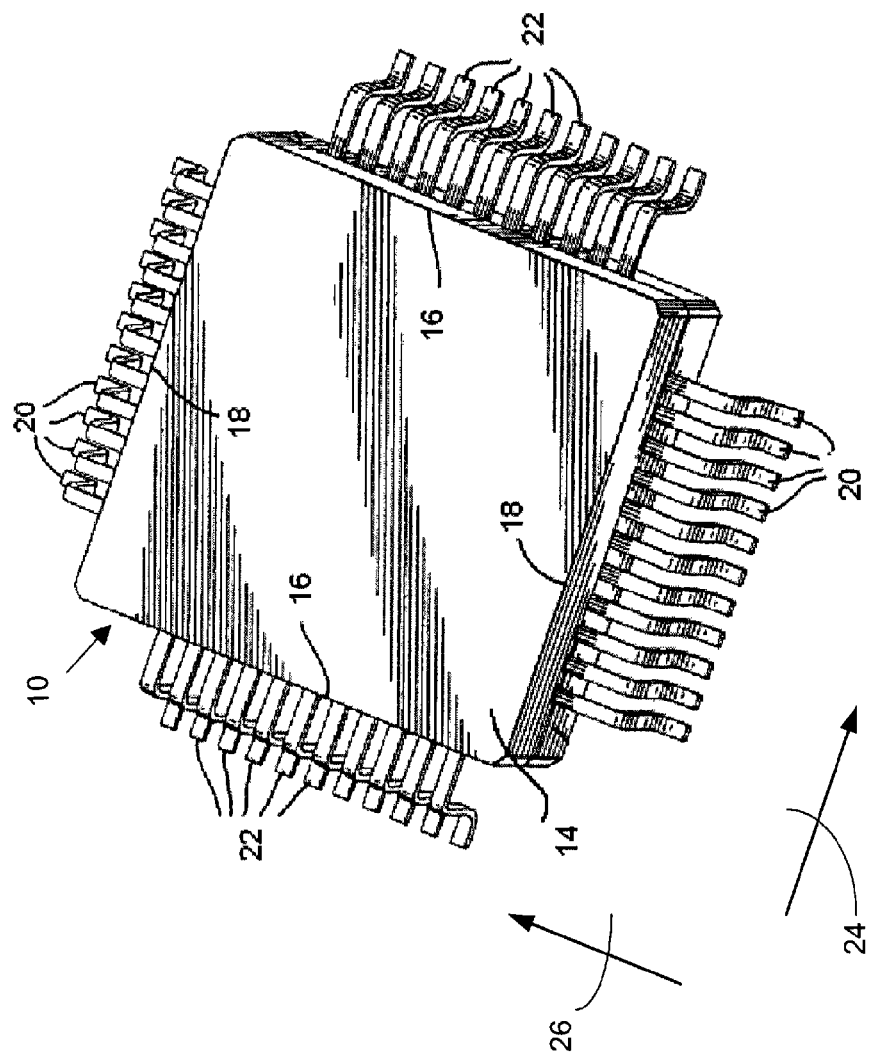
FIG. 1 is a perspective view of a QFP device.
Figure 2:
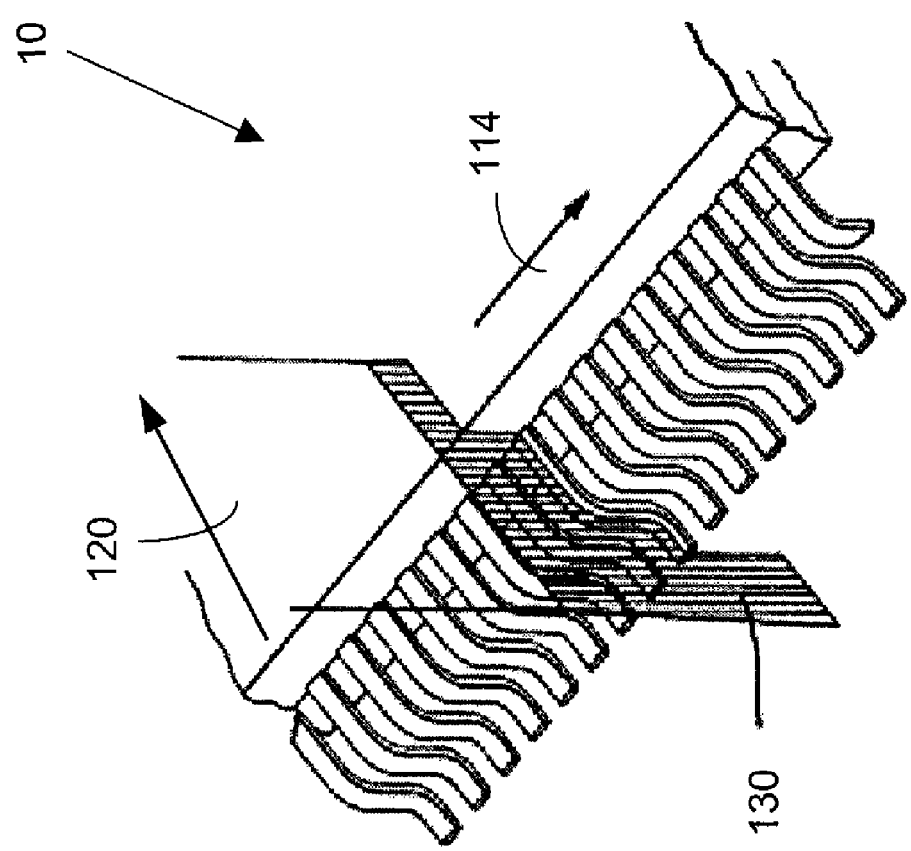
FIG. 2 is a perspective view illustrating how lead profile is determined in accordance with an illustrative embodiment of the present invention.

Referring now to FIGS. 1 and 2, QFP devices as in 10 have a first group of leads 22 extending from a first pair of opposite side edges 16, in a first direction 24, and a second group of leads 20 extending from the second pair of opposite side edges 18, in a second direction 26 transverse to the first direction 24. When inspecting QFP leads 20, 22 using a 3D scanning system (not shown), two distinct scans in a scan direction parallel with lead main axes under inspection (a scan in each direction) are generally required. During the scan, a light plane 130 is projected in the scan direction 120, perpendicularly to the laser head direction 114.

Figure 3:
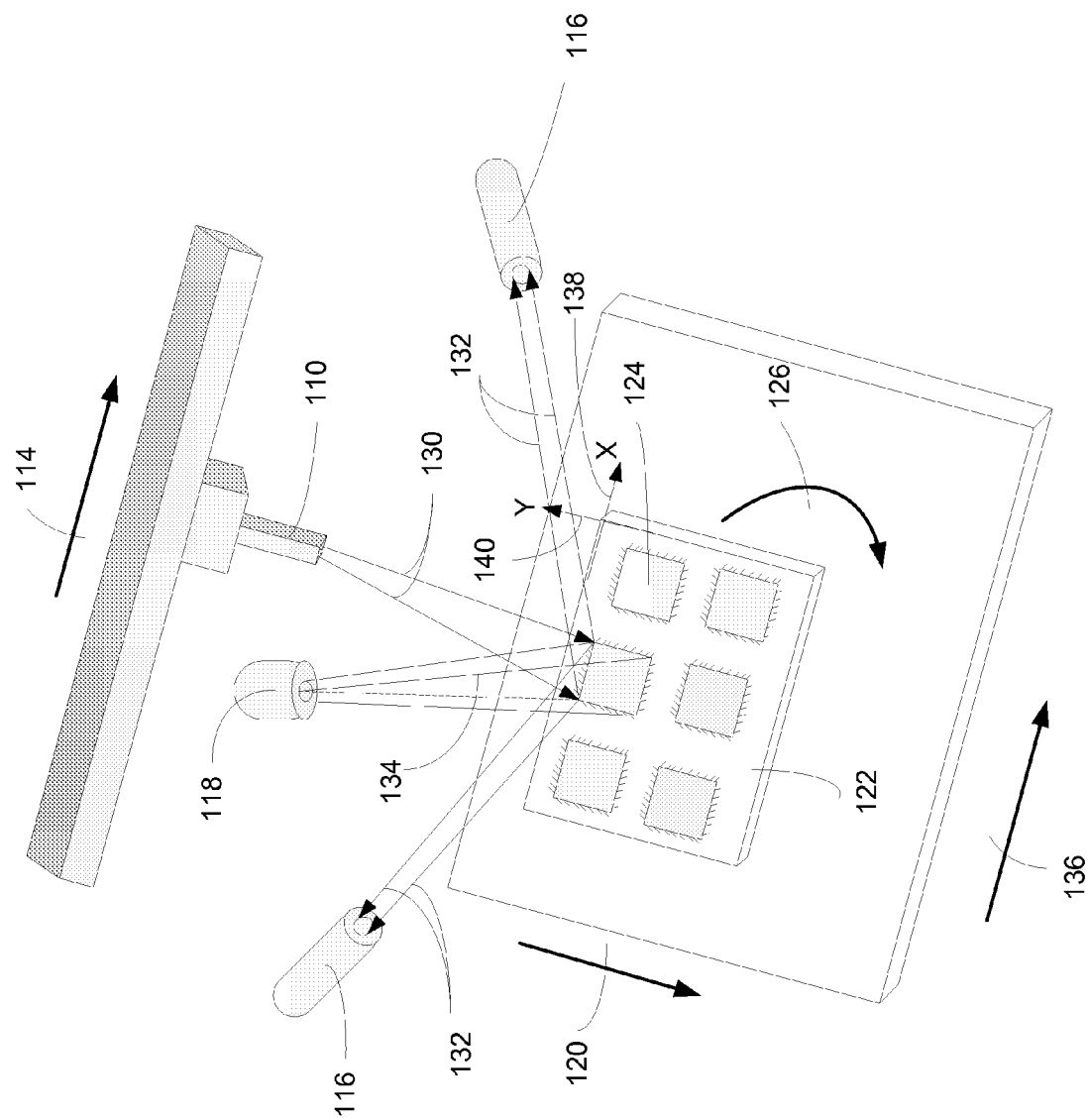
FIG. 3 is a perspective view of an optical inspection system of QFP devices scanning a QFP device in a first direction in accordance with an illustrative embodiment of the present invention.

The present invention provides methods of scanning QFP leads in two directions, while avoiding the drawbacks of prior art techniques. In this approach, the present invention uses, as illustrated in FIG. 3, a single laser triangulation system 110 oriented in a fixed direction 120. In order to switch between two scan directions, the tray 122 in which the QFP devices 124 are placed is illustratively rotated. Accordingly, the tray 122 is fed into the scanner and the QFP devices sitting therein 124 are scanned in a first direction 140. During the scanning process, the tray 122 is immobilized and, in the event the field of view is smaller than the width of the tray, the scanning optics are moved in the laser head direction 114 as well as transversely thereto, in the scan direction 120, to cover the width of the tray. The IC devices thus do not move while the scan in the first direction 140 is in progress.

Figure 4:
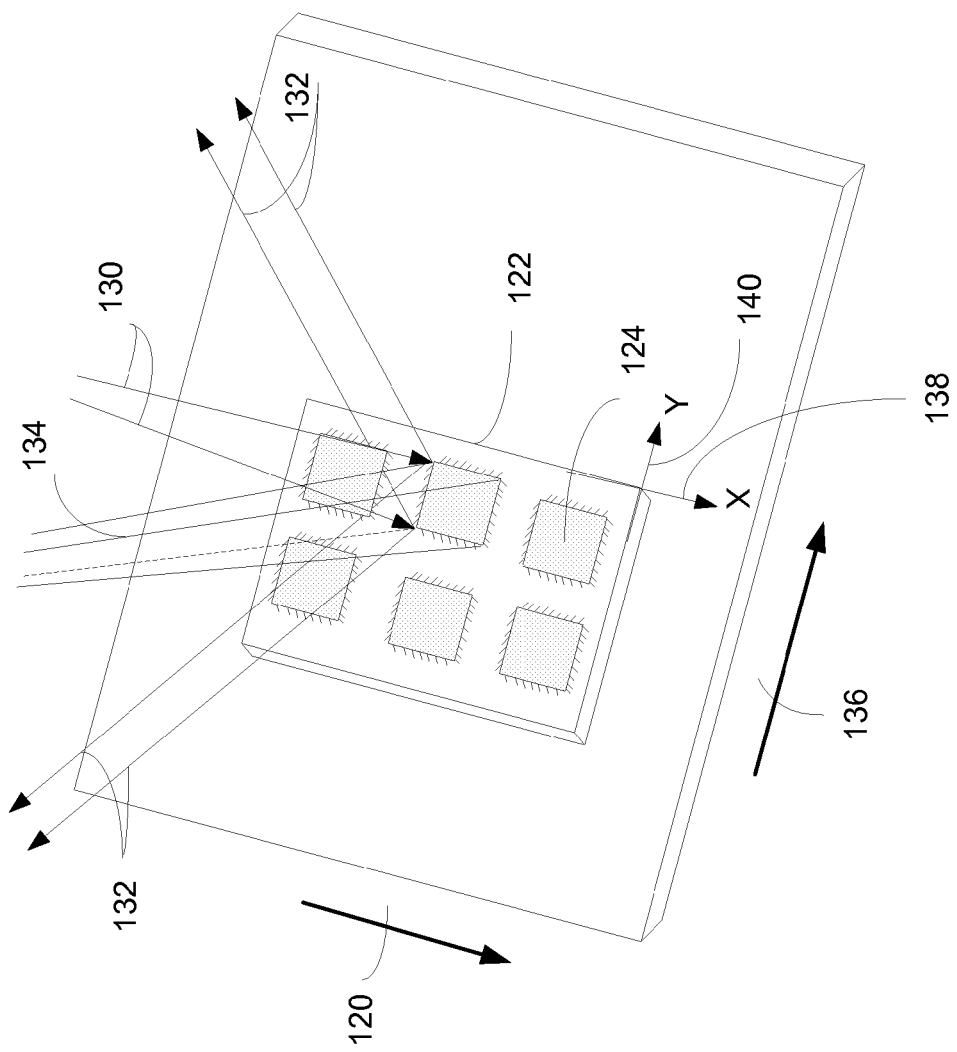
FIG. 4 is a perspective view of an optical inspection system of QFP devices scanning a QFP device in a second direction, after a tray rotation, in accordance with an illustrative embodiment of the present invention.
Figure 5:
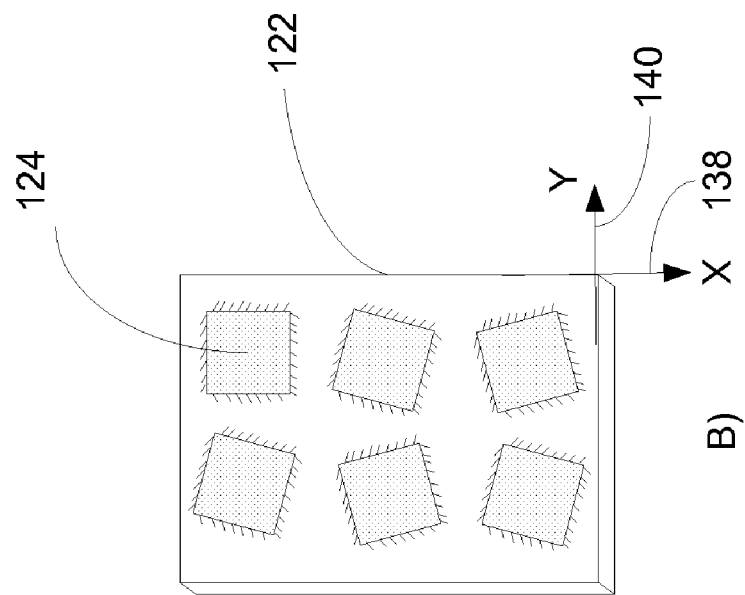
FIG. 5A is a raised perspective view illustrating the position of QFP devices resting in an inspection tray prior to tray rotation.
FIG. 5B is a raised perspective view illustrating displacement of QFP devices resting in an inspection tray following tray rotation.
Figure 5:
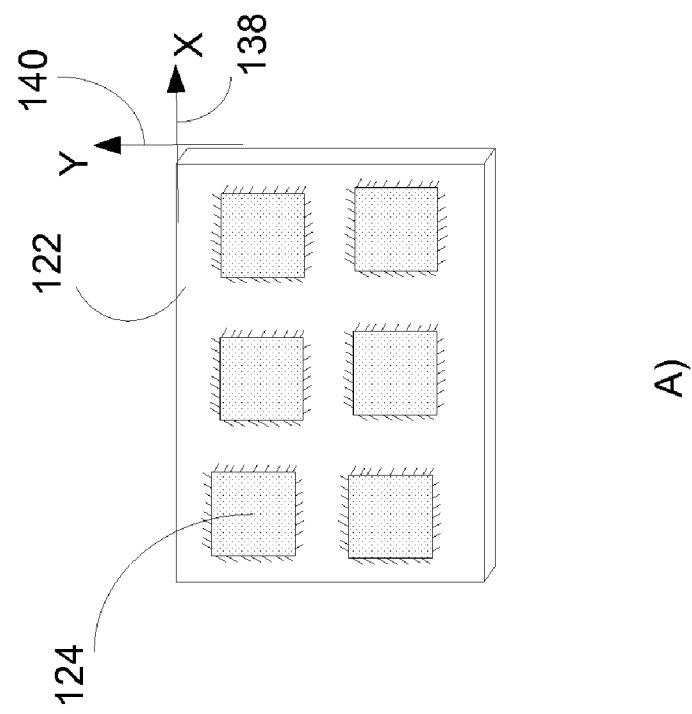

Referring now to FIG. 4 in addition to FIG. 3, the tray 122 is subsequently rotated 90 degrees 126 and the QFP devices 124 are then scanned in a second direction 138. As can be appreciated, time is of the essence when inspection on the manufacturing line is performed. The 90 degree rotation 126 therefore, and with reference to FIGS. 5A and 5B, is carried out rapidly, and as a result the acceleration and deceleration typically result in at least some of the IC devices in the tray being displaced, particularly those farther away from the center of rotation. FIG. 5A illustrates the state of the QFP devices before that the rotation takes place and FIG. 5B illustrates the displacement of the devices resulted by the rotation.

Referring back to FIG. 3, the laser beam 130 projected on the QFP device under inspection 124 is reflected therefrom and the reflected laser 132 is received by at least one 3D camera 116 (two 3D cameras are typically required to overcome the occlusion problems). The first and second scans result respectively in first and second scan data sets. These scan data sets are not immediately combinable because of a mismatch or lack of registration between them, even if the rotation of the tray is precision controlled, due to the likely shift of the devices within the tray due to the rapid rotation (see FIG. 5B). However, the datasets are combined by first identifying a common feature, such as the side edges of each QFP 124 or the like, to obtain a registration vector, and then using the registration vector to combine the two datasets.

The present invention permits thorough inspection of lead characteristics, such as clearance between adjacent leads, bent conditions, overall lead position (geometry) and co-planarity.

Figure 6:
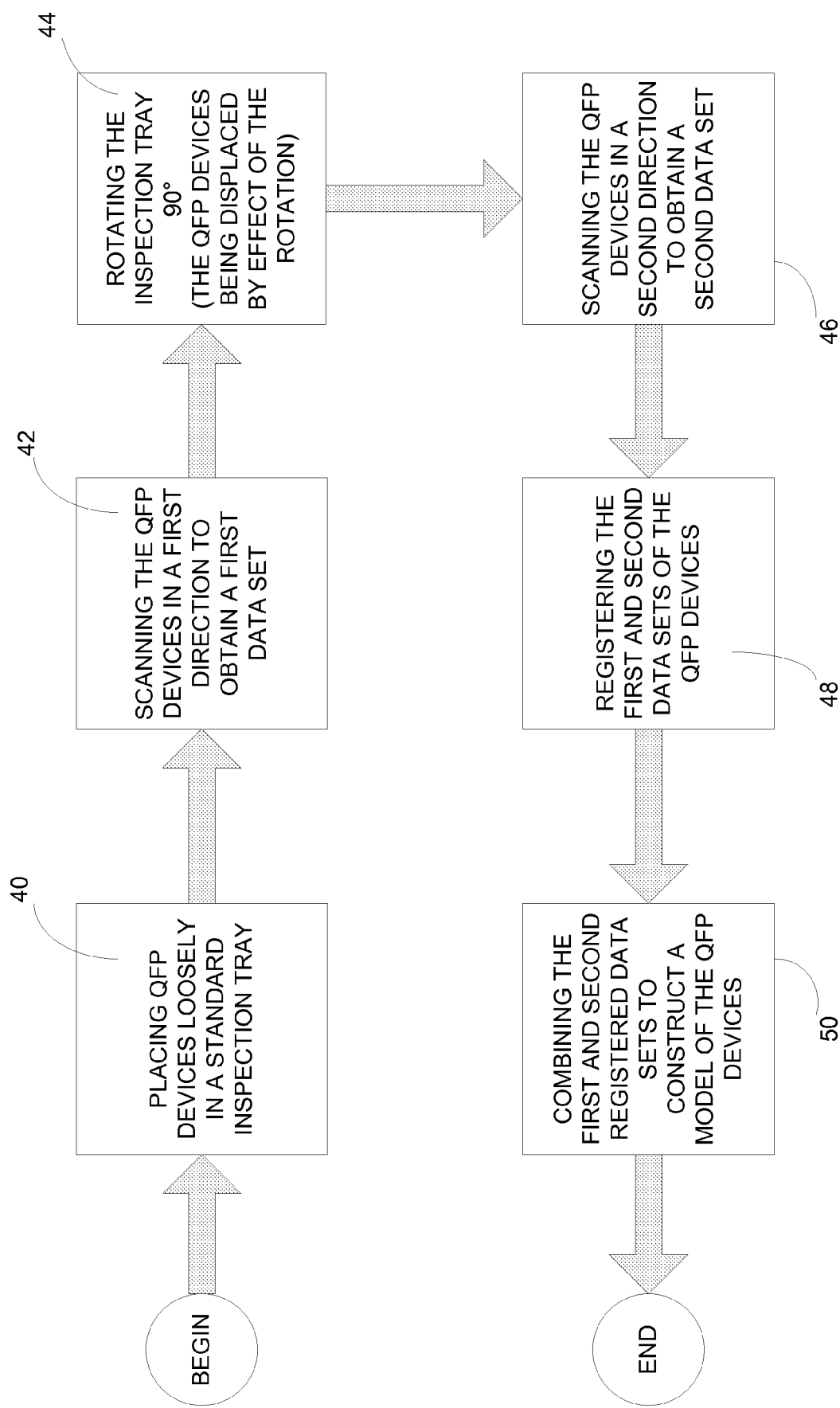
FIG. 6 is a flow chart showing a method of inspecting QFP devices in accordance with an illustrative embodiment of the present invention.

Referring to FIG. 6, there is shown a method of inspecting QFP devices which considers rotating the tray to scan in two directions, where the given method overcomes the problem of device displacement aforementioned.

According to this method, QFP devices 124 to be inspected are first placed loosely inside the pockets of a standard inspection tray 40. Next, the QFP leads extending in a first direction, from the first pair of opposite side edges, are scanned and a first profile line data set is obtained 42. The tray is subsequently rotated 90 degrees 44 and the QFP leads extending in a second direction transverse to the first direction, from the second pair of opposite side edges, are scanned and a second profile line data set is obtained 46.

As discussed above, due to the fact that rotating the tray results usually in displacing the QFP devices sitting in the pockets, generally the two profile line data sets obtained for each QFP are mismatched and cannot be combined accurately. To resolve this problem, the first and the second profile line data sets are registered 48. The registering process involves identifying a common feature in the first and the second profile line data sets and referencing these data sets with respect to the identified common feature. By using a 2D scanning system 118, it is also possible to identify a common feature from a 2D image 134 of the QFP device under inspection. Usually, a common feature consists of at least a part of the side edges of the QFP device under inspection and is obtained by using at least one of the profile line data sets and the 2D image.

Following the registration step, the first and the second profile line data sets referenced with respect to the identified common feature are combined to construct a model of the QFP devices 50. Generally, this model represents the leads of the inspected QFP devices, which permits assessing lead qualities, such as clearance between adjacent leads, bent conditions, overall lead position and co-planarity. The model can illustratively be 3D volumetric data of the leads that can be presented in a 3D graphics model environment, or more primitively and simply a set of lead attribute parameters.

Although the method illustrated in reference to FIG. 6 is for inspecting QFP devices, it can also be used for inspecting any object that needs to be inspected from various directions. During a given inspection, the object can be rotated several times and inspected from various directions. Profile line data sets obtained according to the various directions can subsequently be registered and a model of the inspected object then be constructed.

According to another aspect of the invention, there is provided a method of inspecting various types of integrated circuit devices having leads.

Figure 7:
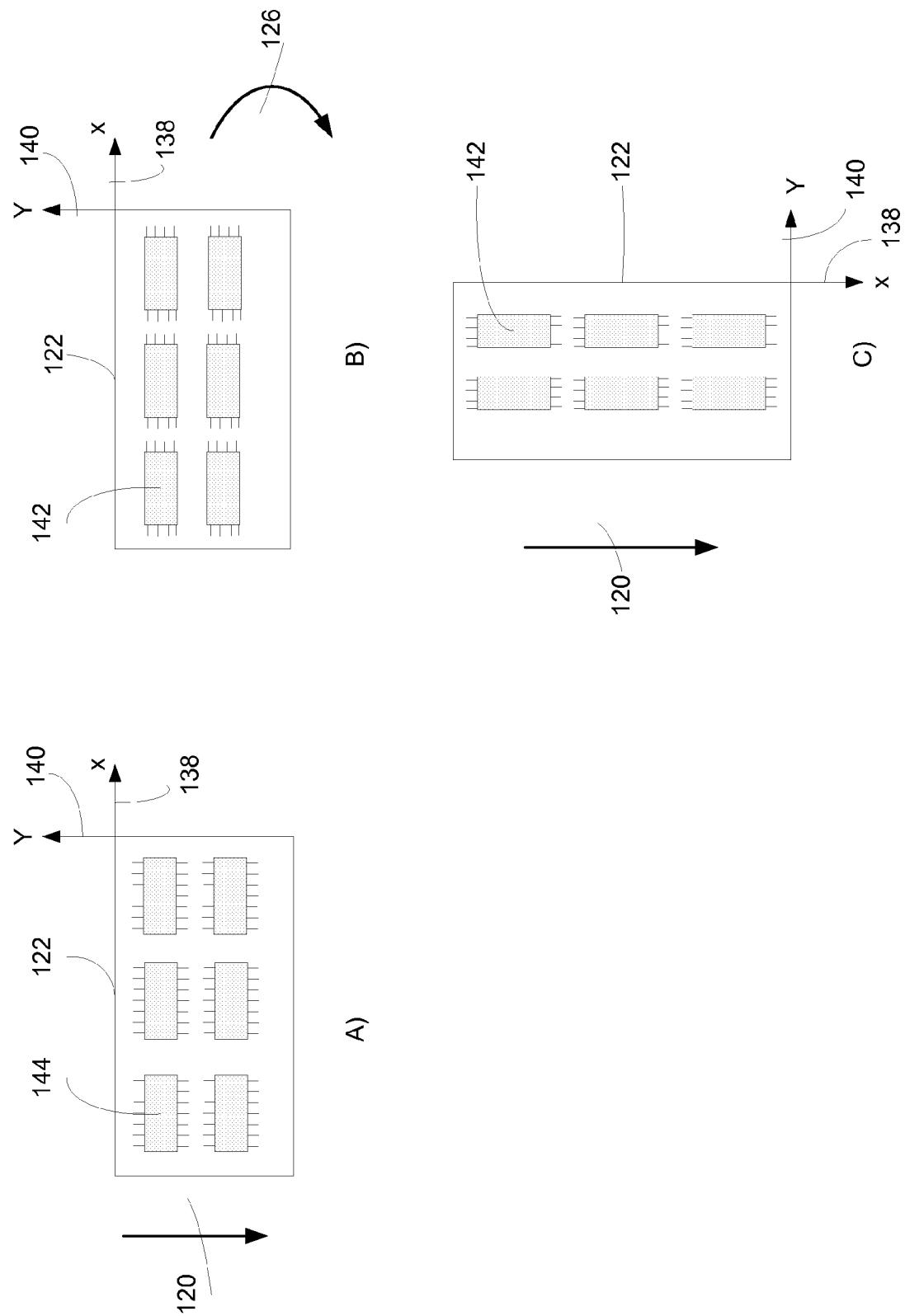
FIG. 7A is a top plan view of an inspection tray containing integrated circuit devices of a first type which have leads extending from the long side edges.
FIGS. 7B and 7C provide top plan views of an inspection tray containing integrated circuit devices of a second type which have leads extending from the short side edges.

Referring now to FIGS. 7A, 7B and 7C, a first type of integrated circuit devices having leads extending from the two long opposite side edges 144 (ex. TSOP II) and a second type of integrated circuit devices having leads extending from the two short opposite side edges 142 (ex. TSOP I) are provided.

In the field of integrated circuit inspection, a standard inspection tray 122 is typically used for various types of devices and it is fed in a fixed orientation 136 inside the inspecting scanner. In fact, the loaded and unloaded tray orientation 136 is the same for all trays regardless of device orientation within the tray. Since the scan direction is preferably parallel to the lead main axes, this means that a tray containing first type IC devices 144 should be scanned in a first direction 140, wherein a tray containing second type IC devices 142 should be scanned in a second direction 138 transverse to the first direction 140.

According to one embodiment, it is possible to inspect sequentially these two types of integrated circuits (TSOP I and TSOP II) using the same apparatus. According to FIGS. 7 and 8, the first type IC devices 144 (ex. TSOP II) are placed in a first standard tray 122 and the latter is placed in a scanner having a 3D scanning system 60. These first type devices are subsequently scanned 62 in a first direction 140 prior to the first tray being removed/unloaded from the scanner 64. Next, the second type IC devices 142 (ex. TSOP I) are placed in a second standard tray 122 and the latter is placed in the scanner 66. The second tray is subsequently rotated 68 by a predetermined angle 126 (ex. 90 degrees in this case but other angles may also prove viable) before the second type devices are scanned 70 in the second direction 138.

This method could be used for other applications, such as a sequential inspection of QFP devices, TSOP I devices and TSOP II devices using the same apparatus. According to this example, after scanning the second type of devices 70 (as shown in FIG. 6), the second tray can be unloaded and the QFP devices inspected according to the method shown in FIG. 8.

Figure 8:
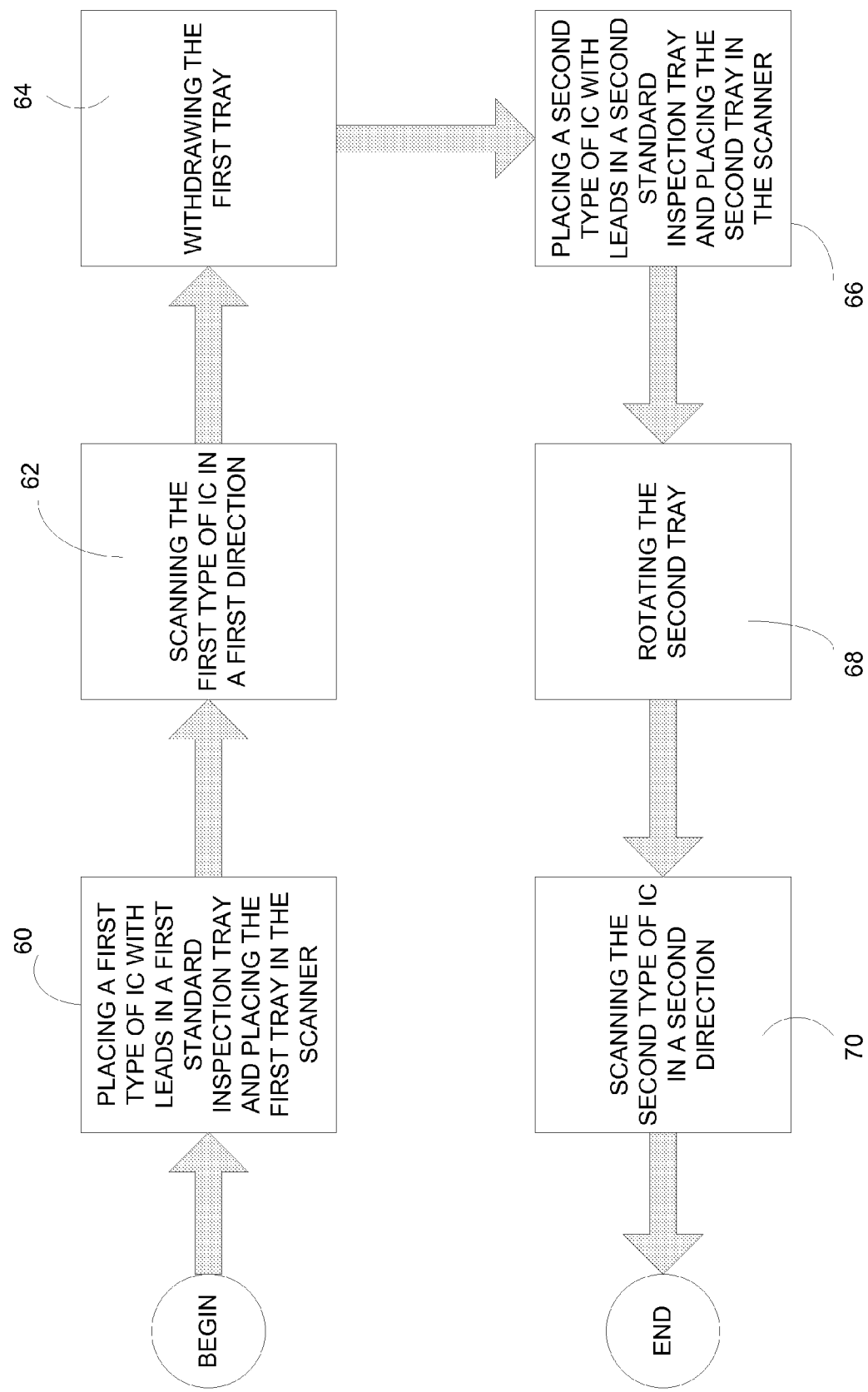
FIG. 8 is a flow chart showing a method of inspecting various types of integrated circuit devices having leads.

The method shown in FIG. 8 can be applied to inspect in a sequential way various types of integrated circuits having leads as required. Furthermore, rotation of the inspection tray 126 can be carried out as many times as wanted before the tray is removed and the rotation angles can have any desired values.

For instance, it is possible to use the method shown in FIG. 8 as follows: TSOP II devices are placed in a first tray and scanned in a first direction following which the first tray is removed. TSOP I devices are subsequently placed in a second tray and the latter is fed into the scanner. The second tray is then rotated 45 degrees with respect to the first direction and the devices scanned in a first direction. The second tray is subsequently rotated −45 degrees with respect to the first direction before the devices are scanned again in a second direction.

After a device has been inspected and a model of the inspected device constructed, the model is used to determine a fitness of the given device and the latter is either recycled or released as a function of the fitness.

While the invention has been described with particular reference to the illustrated embodiments, it will be understood that numerous modifications thereto will appear to those skilled in the art. Accordingly, the above description and accompanying drawings should be taken as illustrative of the invention and not in a limiting sense.

We claim:

1. A method of inspecting an object, the method comprising:

placing the object on a support and placing said support in a scanner comprising a 3D scanning system;

scanning the object in a first direction using said 3D scanning system to obtain a first profile line data set of the object;

rotating said support with respect to said first direction to scan the object in a second direction, said rotation of said support having an effect of displacing the object with respect to said support;

scanning said device in said second direction using said 3D scanning system to obtain a second profile line data set of the object;

identifying a common feature in said first and second profile line data sets of the object;

referencing said obtained first and second profile line data sets with respect to said common feature; and combining said first and second profile line data sets referenced with respect to one another to construct a model of the object.

2. The method as claimed in claim 1, wherein said support is a tray and the object is a QFP device placed loosely in a rectangular pocket within said tray, the QFP device having a rectangular body with four side edges from which leads extend, said second direction is at 90 degrees with respect to said first direction and said model represents leads of the QFP device.

3. The method of claim 2, wherein said identifying a common feature consists of identifying at least a part of said side edges as a common feature.

4. The method of claim 1, wherein said scanner further comprises a 2D scanning system with a 2D field of view, said method further comprises a step of scanning said device using said 2D scanning system to obtain a 2D image of at least a part of said device, said at least a part of said device being located within said 2D field of view and comprising said common feature and said step of identifying a common feature further comprises using at least one of said 2D image and said profile line data sets to identify said common distinctive feature.

5. The method of claim 4, wherein said support is a tray and said object is a QFP device placed loosely in a rectangular pocket within said tray, said QFP device having a rectangular body with four side edges from which leads extend, said second direction is at 90 degrees with respect to said first direction and said model represents leads of said QFP device.

6. The method of claim 5, wherein said identifying a common feature consists of identifying at least a part of said side edges as a common feature.

7. A method of inspecting an integrated circuit comprising a rectangular package and leads arranged along a first and second non-parallel edges, the method comprising:

placing the integrated circuit in a scanner comprising a 3D scanning system;

scanning the leads along the first edge in a first direction using said 3D scanning system to obtain a first profile line data set of the object;

rotating the integrated circuit with respect to said first direction to scan the object in a second direction;

scanning the leads along the second edge in said second direction using said 3D scanning system to obtain a second profile line data set of the integrated circuit;

identifying a common feature in said first and second profile line data sets of the integrated circuit;

referencing said obtained first and second profile line data sets with respect to said common feature; and combining said first and second profile line data sets referenced with respect to one another to construct a model of the integrated circuit.

8. The method of claim 7, wherein said placing act comprises placing the integrated circuit on a support and placing said support in said scanner and further wherein said rotating act comprises rotating said support, said rotation of said support having an effect of displacing the object with respect to said support.

9. A method of inspecting different types of integrated circuit devices having leads, the method comprising:

providing a scanner comprising: a 3D scanning system having a predetermined scan direction and a tray manipulation system for receiving a tray of predetermined rectangular dimensions and orientation carrying integrated circuit devices, positioning said tray within said 3D scanning system, and for transferring said tray from said scanner to a downstream tray handling device following inspection;

using said tray manipulation system to place a first tray containing a first type of integrated circuit devices having leads in said scanner, and scanning said first type of devices in a first direction with said 3D scanning system operating in said predetermined scan direction;

removing said first tray from said scanner using said tray manipulation system;

using said tray manipulation system to place a second tray containing a second type of integrated circuit devices in said scanner and to rotate said second tray, and scanning said second type of devices in a second direction with said 3D scanning system operating in said predetermined scan direction;

removing said second tray from said scanner, said tray manipulation system transferring said first tray and said second tray to said downstream tray handling device in a same orientation.

10. The method of claim 9, wherein said first type of integrated circuit devices are QFP devices and said scanning said first type of devices further comprises rotating said first tray 90° with respect to said first direction and scanning said QFP devices in a third direction transverse to said first direction.

11. The method of claim 9, wherein said first type of integrated circuit devices are TSOP devices having leads extending in said first direction with respect to said tray orientation, said second type of integrated circuit devices are TSOP devices having leads extending substantially in said second direction with respect to said tray orientation and said first direction is transverse to said second direction.

12. The method of claim 11, wherein said rotating said second tray consists of rotating said second tray 90° with respect to said first direction.

13. The method of claim 11, wherein said angle between said scan direction and said tray orientation is 45 degrees, said first tray is rotated 45 degrees in said first direction of rotation to scan said object in said first direction and said second tray is rotated 45 degrees in said second direction of rotation opposite to said first direction of rotation to scan said object in said second direction transverse to said first direction.

14. The method of claim 9, wherein said scan direction is at an angle with respect to said tray orientation, said first tray is rotated prior to scanning in a first direction of rotation and said second tray is rotated prior to scanning in a second direction of rotation opposite to said first direction of rotation.

15. A method of manufacturing a product, the method comprising:

placing said object on a support and placing said support in a scanner comprising a 3D scanning system;

scanning said object in a first direction using said 3D scanning system to obtain a first profile line data set of said object;

rotating said support with respect to said first direction to scan said object in a second direction, said rotation of said support having an effect of displacing said object with respect to said support;

scanning said device in said second direction using said 3D scanning system to obtain a second profile line data set of said object;

identifying a common feature in said first and second profile line data sets of said object;

referencing said obtained first and second profile line data sets with respect to said common feature;

combining said first and second profile line data sets referenced with respect to one another to construct a model of said object;

determining from said model a fitness of said product; and recycling or releasing said product as a function of said fitness.

16. A method of manufacturing different types of products, the method comprising:

providing a scanner comprising: a 3D scanning system having a predetermined scan direction and a tray manipulation system for receiving a tray of predetermined rectangular dimensions and orientation carrying integrated circuit devices, positioning said tray within said 3D scanning system, and for transferring said tray from said scanner to a downstream tray handling device following inspection;

using said tray manipulation system to place a first tray containing a first type of products in said scanner, and scanning said first type of products in a first direction with said 3D scanning system operating in said predetermined scan direction, where said first type of products are a first type of integrated circuit devices having leads;

constructing a model of said first type of products;

determining from said model a fitness of said first type of products;

recycling or releasing said first type of products as a function of said fitness;

removing said first tray from said scanner using said tray manipulation system;

using said tray manipulation system to place a second tray containing a second type of products in said scanner and to rotate said second tray, and scanning said second type of products in a second direction with said 3D scanning system operating in said predetermined scan direction, where said second type of products are a second type of integrated circuit devices having leads;

constructing a model of said second type of products;

determining from said model a fitness of said second type of products;

recycling or releasing said second type of products as a function of said fitness;

removing said second tray from said scanner, said tray manipulation system transferring said first tray and said second tray to said downstream tray handling device in a same orientation.

* * * * *